United States Patent
Wasserscheid et al.

(10) Patent No.: US 7,691,180 B2
(45) Date of Patent: Apr. 6, 2010

(54) MIXTURES OF IONIC LIQUIDS WITH LEWIS ACIDS

(75) Inventors: Peter Wasserscheid, Erlangen (DE); Andreas Metlen, Erlangen (DE); Nicole Brausch, Erlangen (DE)

(73) Assignee: Novartis AG, Basel (CH)

( * ) Notice: Subject to any disclaimer, the term of this patent is extended or adjusted under 35 U.S.C. 154(b) by 959 days.

(21) Appl. No.: 10/564,258

(22) PCT Filed: Jul. 16, 2004

(86) PCT No.: PCT/EP2004/007952

§ 371 (c)(1), (2), (4) Date: Jun. 21, 2006

(87) PCT Pub. No.: WO2005/014547

PCT Pub. Date: Feb. 17, 2005

(65) Prior Publication Data

US 2006/0264642 A1    Nov. 23, 2006

Related U.S. Application Data

(60) Provisional application No. 60/487,957, filed on Jul. 17, 2003.

(51) Int. Cl.
  *B01D 53/22* (2006.01)
  *B01D 19/00* (2006.01)
  *B01J 31/00* (2006.01)

(52) U.S. Cl. .............................. 95/46; 95/241; 95/266; 502/159

(58) Field of Classification Search .................. 502/159; 95/46, 241, 266
    See application file for complete search history.

(56) References Cited

U.S. PATENT DOCUMENTS

| 6,673,737 | B2 * | 1/2004  | Mehnert et al.  | 502/159 |
| 7,166,724 | B2 * | 1/2007  | Hilarius et al. | 548/110 |
| 7,208,605 | B2 * | 4/2007  | Davis, Jr.      | 548/110 |
| 7,303,607 | B2 * | 12/2007 | Tempel et al.   | 95/241  |

FOREIGN PATENT DOCUMENTS

| FR | 2829763       | 9/2001 |
| FR | 2 829 763     | 3/2003 |
| WO | 02/072260     | 9/2002 |
| WO | WO 02/072260  | 9/2002 |

OTHER PUBLICATIONS

Zulfiqar, et al, "Lewis Acid-Catalyzed Sequential Reaction in Ionic Liquids", Green Chemistry, pp. 296-297 (2000).
Zulfiqar, et al: "Lewis acid-catalysed sequential reaction in ionic liquids", Green Chemistry, pp. 296-297, 2000.

* cited by examiner

*Primary Examiner*—Janet L. Andres
*Assistant Examiner*—Raymond Covington
(74) *Attorney, Agent, or Firm*—Sandra S. Shim

(57) ABSTRACT

Ionic liquids comprising a mixture of one or more triflate or bis(trifluoromethylsulfonyl)imide salt(s) with one or more Lewis acids(s), wherein the total of the molar contents of the Lewis acid(s) in the mixture is from about 0.01-98%, are provided, that are useful as catalysts in Lewis acid catalyzed reactions.

9 Claims, No Drawings

MIXTURES OF IONIC LIQUIDS WITH LEWIS ACIDS

This application claims benefit of U.S. Provisional Application 60/487,957, filed Jul. 17, 2003.

FIELD OF THE INVENTION

New ionic liquid materials which are mixtures of a triflate or bis(trifluoromethylsulfonyl)imide salt of an imidazolium, pyridinium, ammonium, or phosphonium ion with the Lewis acids ($AlCl_3$, $AlBr_3$, $SnCl_2$, $FeCl_3$, and $ZnCl_2$).

BACKGROUND OF THE INVENTION

Friedel-Crafts reactions (acylation and alkylation) are among the basic reactions used to synthesize functionalized aromatic compounds, which are extremely important intermediates for pharmaceutical products and fine chemicals. Prior-art liquid and solid Lewis and Brønsted acids are used as catalysts for Friedel-Crafts reactions.

The acidity of the catalyst affects the reaction kinetics of Friedel-Crafts reactions in many ways. For instance, the stronger the acidity of the catalysts, more easily deactivated aromatic compound can be used. The higher acidity also results in an improved reaction selectivity, for example in Fries rearrangement reactions. The usual acids in the chemical industry today are sulfuric acid and $AlCl_3$, In various modifications.

An acidic reactant also known is an acidic ionic liquid, which is a salt having a melting point of less than 100° C., can be used in Friedel-Crafts reactions as well. The systems employed to date are those formed by adding a molar excess of a Lewis acid to the halide salt of an imidazolium, pyridinium, ammonium, or phosphonium ion. One example is a mixture of Imidazolium chloride salt with a molar excess of $AlCl_3$. These acidic chloroaluminate molten substances are used to catalyze organic reactions in place of solid $AlCl_3$, so that the disadvantage of the low solubility of $AlCl_3$ in most organic solvents Is minimized. Examples in the literature include the reaction of benzene and toluene with various alkyl chlorides in a mixture of 1-ethyl-3-methylimidazolium chloride ([EMIM]Cl) and $AlCl_3$ (4 parts [EMIM]Cl/6 parts $AlCl_3$); and the alkylation of benzene with ethylene to form ethylbenzene using a liquid catalyst phase that is a mixture of an imidazolium chloride salt having a molar excess of $AlCl_3$ or a molar excess of $GaCl_3$.

An early example of a Friedel-Crafts acylation in an ionic liquid used a mixture of an imidazolium chloride salt with a molar excess of $AlCl_3$ as a catalytically active phase, also describing that the rate of reaction increased with the increase of the percentage of the Lewis acid $AlCl_3$ in the mixture.

The synthesis of some industrially important fragrance compounds (for example: Traseolid®) by means of Friedel-Crafts acylation in an acidic mixture of [EMIM]Cl-$AlCl_3$(X ($AlCl_3$)=0.67) has also been described. Again, an acceleration of the reaction was observed when the percentage of $AlCl_3$ was increased further in the mixture. However, in the [EMIM]Cl-$AlCl_3$, the molar percentage of $AlCl_3$ cannot be increased beyond 67% molar, since at a higher $AlCl_3$ content the melting point of the mixture climbs beyond 100° C.

Other reactions studied include the acylation of naphthalene and anthracene; the cracking of polyethylene; and the isomerization of fatty acids; all performed in acidic chloroaluminate melts.

The use of the Lewis acid $FeCl_3$ to form acidic ionic liquids in the system [EMIMI]Cl-$FeCl_3$ has also been described. Here too, an excess of Lewis acid is used, although only mixtures that have a molar $FeCl_3$ content of less than 62% are liquid at temperatures below 100° C. The acylation of benzene with acyl chloride has been described, wherein the ketone that is formed is separated from the catalyst phase by means of extraction, when the molar $FeCl_3$ content in the catalytically active mixture lies between 51 and 55 mol %.

In addition to the catalytically active ionic liquids that are formed by combining an excess of a Lewis acid with an organic chloride salt, a small number of other examples have been described in which Lewis acids such as scandium (III) triflate and other lanthanoid salts were mixed with a neutral ionic liquid containing $[PF_6]^-$, $[BF_4]^-$, $[SbF_6]^-$, or triflate ion in order to obtain a catalytically active system. However, in all such systems the Lewis acid is used at very low levels relative to the ionic liquid. Typically, mixtures have molar ratios of one part Lewis acid to 27 parts neutral ionic liquid. The resulting systems have been used to alkylate benzene with 1-hexene.

Mixtures of lanthanoid triflate salts and neutral ionic liquid containing $[PF_6]^-$, $[BF_4]^-$, $[SbF_6]^-$, or triflate ion have also been described in which the lanthanoid is used as a Lewis acid at a very low molar ratio relative to the ionic liquid. The molar ratio between the lanthanoid triflate and the ionic liquid is typically 1:200. These mixtures have been used to achieve a 3-component synthesis of α-aminophosphonates. An important limitation in the industrial usefulness of the concept is the known decomposition of labile complex anions (such as $[PF_6]^-$, $[SbF_6]^-$,)) in the presence of strong Lewis acids.

Fundamentally different, catalytically active, acidic Ionic liquids have been developed and used, for example, in the Friedel-Crafts alkylation of benzene with decene. Examples include an ionic liquids which are mixtures of [BMIM] $[HSO_4]$ and the Brønsted acid sulfuric acid, substantially free of Lewis acidity; these mixtures were unable to achieve an acidity exceeding that of pure sulfuric acid.

Other acidic ionic liquids based on a similar concept include a mixture of tributylhexylammonium-bis(trifluoromethanesulfonyl)imide ($[NBu_3(C_6H_{13})][(CF_3SO_2)_2N]$) and a Brønsted acid in acid-catalyzed cyclization reactions. Phosphoric acid and toluene sulfonic acid have also been used as Brønsted acids. However, there is a problem in that if even stronger Brønsted acids are added to a bis(trifluoromethanesulfonyl)amide melt, the free acid of the anion is formed, which sublimates easily at low temperatures.

In general, it can be seen from the previously disclosed uses of acidic Ionic liquids in various acid-catalyzed reactions that the use of acidic, liquid salts as catalysts is promising from an industrial point of view. The prior-art acidic ionic liquids possess variable acidity in certain ranges and interesting solubility characteristics that can be varied by the nature of the cation. These solubility characteristics allow new approaches to the industrial implementation of acid-catalyzed reactions, for example by using a multiple-phase reaction regime.

DESCRIPTION AND SUMMARY OF THE INVENTION

This Invention relates to the production of new unexpected ionic liquid materials which are mixtures of a triflate or bis (trifluoromethylsulfonyl)imide salt of an imidazolium, pyridinium, ammonium, or phosphonium ion with the Lewis acids ($AlCl_3$, $AlBr_3$, $SnCl_2$, $FeCl_3$, and $ZnCl_2$), when the molar mixing ratio between the Lewis acid and the triflate or bis(trifluoromethylsulfonyl)amide salt of the imidazolium, pyridinium, ammonium, or phosphonium ion is greater than 1:1. These materials are liquids at temperatures below In one embodiment of the invention, the materials have molar ratios of up to 4.5/1 Lewis acid/triflate or Lewis acid/bis(trifluoromethysulfonyl)amide salts of the imidazolium, pyridinium, ammonium, or phosphonium ion in liquid mixtures at temperatures below 100° C.

This Invention also relates to mixtures of a number of different triflate of bis(trifluoromethylsulfonyl)imide salts mixed with mixtures of various Lewis acids of the group comprising $AlCl_3$, $AlBr_3$, $SnCl_2$, $FeCl_3$, and $ZnCl_2$. The molar content of the Lewis-acidic components that are used can exceed 50 mol % of the total mixture, preferably they can exceed 67 mol % of the total mixture.

The new acidic ionic liquids of this invention are prepared by mixing an imidazolium, pyridinium, ammonium, or phosphonium triflate or bis(trifluoromethylsulfonyl)amide salt or a mixture of a plurality of imidazolium pyridinium, ammonium, or phosphonium triflate or bis(trifluoromethylsulfonyl) amide salts with a molar excess of a Lewis acid of the group comprising $AlCl_3$, $AlBr_3$, $SnCl_2$, $FeCl_3$, and $ZnCl_2$ or with a molar excess of a mixture of the aforesaid Lewis acids. Preferably, the imidazolium, pyridinium, ammonium, or phosphonium triflate or bis(trifluoromethylsulfonyl)amide salt or the mixture of a plurality of imidazolium, pyridinium, ammonium, or phosphonium triflate or bis(trifluoromethylsulfonyl) amide salts is mixed with a Lewis acid of the group comprising $AlCl_3$, $AlBr_3$, $SnCl_2$, $FeCl_3$, and $ZnCl_2$ in order to obtain a mixture in which the content of the Lewis acid exceeds 67 mol %. The melting point of the materials obtained in this way Is generally below 25° C.; all examples are below 100° C. in this invention.

The difference relative to the known acidic ionic liquids described in the prior art relates to the industrial usefulness of the novel acidic ionic liquids of this invention as regards the following relevant advantages:

In contrast to the prior-art systems, which are formed by adding a molar excess of a Lewis acid to the halide salt of an imidazolium, pyridinium, ammonium, or phosphonium ion, the novel acidic ionic liquid of this invention is characterized by the following advantages:

I) The novel ionic liquids of this invention are also formed by mixtures of a Lewis acid of the group comprising $AlCl_3$, $SnCl_2$, $FeCl_3$, and $ZnCl_2$ with a imidazolium, pyridinium, ammonium, or phosphonium triflate or bis(trifluoromethylsulfonyl)amide salt in a ratio of >2:1, while none of the prior-art systems obtained from a mixture of a Lewis acid with a halide salt permits a ratio of >2:1, since in the latter case the mixture would have melting points of greater than 100° C. Since the achievable mixing ratio directly correlates with the total acidity of the system, but since the total acidity correlates with the activity and selectivity of the system in an acid-catalyzed reaction, the achievement of higher percentages of the Lewis acid used In the systems of this invention eliminates a previously existing, substantial limitation on the range of applicability of the prior-art acidic, Ionic liquids.

II) In reactions In which the product mixture must be processed hydrolytically (for example, with Friedel-Crafts acylations or other reactions in which molecules containing oxygen or in which nitrogen functionalities are present in the molecule) for the first time the novel acidic ionic liquids of this invention permit the recycling of expensive cation components. Following the hydrolysis, the Imidazolium, pyridinium, ammonium, or phosphonium triflate of bis(trifluoromethylsulfonylyamide salt that is used or the mixture of the imidazolium, pyridinium, ammonium, or phosphonium triflate of bis(trifluoromethylsulfonyl)amide salts with the products can be isolated from the aqueous phase by means of extraction and reused following distillation or crystallization of the reaction products. Thus, the novel ionic liquids of this invention for the first time provide an efficient process for isolating and recovering the relatively expensive cation that is used in the ionic liquid. The loss of the relatively expensive cation in the ionic liquid represents a substantial cost factor in the previously used prior-art processes.

In contrast to the previously known systems, which are formed by mixing a lanthanoid triflate salt with a neutral organic liquid containing $[PF_6]^-$, $[BF_4]^-$, $[SbF_6]^-$, or triflate ions, the following advantages result when the novel, acid ionic liquids of this invention are used:

III) In none of the prior-art systems was it possible to use the Lewis acid (the lanthanoid triflate salt) in a stoichiometric ratio or even a super-stoichiometric ratio relative to the neutral melt, which severely limited the acidity that could be achieved. In contrast, the novel ionic liquids of this invention are formed by mixtures of one or more Lewis acids of the group comprising $AlCl_3$, $SnCl_2$, $FeCl_3$, and $ZnCl_2$ with one or more imidazolium, pyridinium, ammonium, or phosphonium triflate or bis(trifluoromethylsulfonyl)amid salt even in a molar ratio of >2:1.

IV) While the ionic liquids used in the prior art, and here in particular, the anions $[PF_6]^-$, $[BF_4]^-$, $[SbF6]^-$, are known to be unstable in the presence of strong Lewis acids, the novel acidic ionic liquids of this invention are characterized by a much higher stability, even at a much higher molar content of the Lewis acid or acids that are used.

In contrast to the prior-art systems that are formed by mixing a Brønsted acid with an ionic liquid containing an $[HSO_4]$ or $[(CF_3SO_2)_2N]$ ion the following advantages result when the novel, acidic ionic liquids of this invention are used:

V) The novel systems of this invention are Lewis acid systems, while Brønsted acid systems are obtained by mixing a Brønsted acid with an ionic liquid containing an $[HSO_4]$ or $[(CF_3SO_2)_2N]$ ion in the state of the art. However, many applications can only be achieved by using the Lewis acid systems.

VI) The achievable acidity and achievable percentage of active, acidic components in the reaction system, as well as general ease of use, is severely limited in the prior-art systems by the fact that the anion of the ionic liquid (for example $[(CF_3SO_2)_2N]$) forms the volatile acid-$H[(CF_3SO_2)_2N]$ in the presence of strong acids. The volatile acid easily sublimates out of the reaction mixture, which severely limits the range of applicability of the prior-art ionic liquids. Such problems do not occur with the novel, acidic ionic liquids of this invention.

The range of application of the novel acidic ionic liquids of this Invention Includes all reactions in which strong Lewis acids are used as catalysts or in which a strong Brønsted acid is formed under the reaction conditions in the presence of a strong Lewis acid. Particularly suitable applications for the novel acidic ionic liquids of this invention are found wherever an increase in acidity compared with the previously used prior-art systems would result in an improvement in activity, selectivity, or life of the catalytically active component. Specific examples of applications in which the novel, acidic, ionic liquid of this invention can be used successfully comprise, among others, Friedel-Crafts reactions (alkylation and acylation), the Fries rearrangement, carbonylation of aromatic compounds, the isomerization of chlorotoluenes, the isomerization of dichlorobenzenes, the transalkylation of toluene, the framework isomerizations of alkanes, as well as the so-called refinery alkylation (reaction of isobutene with propane or butane to produce alkylate gasoline), whereby this enumeration is not claimed to be complete nor exclusive.

One particularly interesting embodiment of the novel, acidic ionic liquid of this invention results from the unexpected discovery in some mixing ratios between the Lewis acid that is used or the mixture of a plurality of Lewis acids that are used with the triflate or bis(trifluoromethylsulfonyl)imide salt or with the mixture of a plurality of triflate of bis(trifluoromethylsulfonyl)imide salts that the novel, acidic ionic liquids of this invention are present in the form of a liquid-liquid multiple phase system. This opens up new possibilities for processing reaction mixtures and product mixtures by means of extractive methods.

Especially preferred embodiments of the novel, acid ionic liquids of this invention, comprise the following mixtures:

- 1-Methylpyridinium-bis(trifluoromethylsulfonyl)imide with $AlCl_3$
- 1-Ethylpyridinium-bis(trifluoromethylsulfonyl)imide with $AlCl_3$
- 1-Butylpyridinium-bis(trifluoromethylsulfonyl)imide with $AlCl_3$
- 1,4-Dimethylpyridinium-bis(trifluoromethylsulfonyl) imide with $AlCl_3$
- 1,3-Dimethylpyridinium-bis(trifluoromethylsulfonyl) imide with $AlCl_3$
- 1-Ethyl-4-methylpyridinium-bis(trifluoromethylsulfonyl) imide with $AlCl_3$
- 1-Ethyl-3-methylpyridinium-bis(trifluoromethylsulfonyl) imide with $AlCl_3$
- 1-Butyl-3-methylpyridinium-bis(trifluoromethylslfonyl) imide with $AlCl_3$
- 1-Butyl-3-methylpyridinium-bis(trifluoromethylsulfonyl) imide with $AlCl_3$
- 1,3-Dimethylimidazolium-bis(trifluoromethylsulfonyl) imide with $AlCl_3$
- 1-Ethyl-3-methylimidazolium-bis(trifluoromethylsulfonyl)imide with $AlCl_3$
- 1,3-Diethylimidazolium-bis(trifluoromethylsulfonyl) imide with $AlCl_3$
- 1-Butyl-3-methylimidazolium-bis(trifluoromethylsulfonyl)imide with $AlCl_3$
- 1-Butyl-3-ethylimidazolium-bis(trifluoromethylsulfonyl) imide with $AlCl_3$
- Trimethylammonium-bis(trifluoromethylsulfonyl)imide with $AlCl_3$
- Tetramethylammonium-bis(trifluoromethylsulfonyl) imide with $AlCl_3$
- Tetrabutylammonium-bis(trifluoromethylsulfonyl)imide with $AlCl_3$
- Tetrabutylphosphonium-bis(trifluoromethylsulfonyl) imide with $AlCl_3$
- 1-Methylpyridinium triflate with $AlCl_3$
- 1-Ethylpyridinium triflate with $AlCl_3$
- 1-Butylpyridinium triflate with $AlCl_3$
- 1,4-Dimethylpyridinium triflate with $AlCl_3$
- 1,3-Dimethylpyridinium triflate with $AlCl_3$
- 1-Ethyl-4-methylpyridinium triflate with $AlCl_3$
- 1-Ethyl-3-methylpyridinium triflate with $AlCl_3$
- 1-Butyl-4-methylpyridinium triflate with $AlCl_3$
- 1-Butyl-3-methylpyridinium triflate with $AlCl_3$
- 1,3-Dimethylimidazolium triflate with $AlCl_3$
- 1-Ethyl-3-methylimidazolium triflate with $AlCl_3$
- 1,3-Diethylimidazolium triflate with $AlCl_3$
- 1-Butyl-3-methylimidazolium triflate with $AlCl_3$
- 1-Butyl-3-ethylimidazolium triflate with $AlCl_3$
- Trimethylammonium triflate with $AlCl_3$
- Tetramethylammonium triflate with $AlCl_3$
- Tetrabutylammonium triflate with $AlCl_3$
- Tetrabutylphosphonium triflate with $AlCl_3$
- 1-Methylpyridinium-bis(trifluoromethylsulfonyl)imide with $FeCl_3$
- 1-Ethylpyridinium-bis(trifluoromethylsulfonyl)imide with $FeCl_3$
- 1-Butylpyridinium-bis(trifluoromethylsulfonyl)imide with $FeCl_3$
- 1,4-Dimethylpyridinium-bis(trifluoromethylsulfonyl) imide with $FeCl_3$
- 1,3-Dimethylpyridinium-bis(trifluoromethylsulfonyl) imide with $FeCl_3$
- 1-Ethyl-4-methylpyridinium-bis(trifluoromethylsulfonyl) imide with $FeCl_3$
- 1-Ethyl-3-methylpyridinium-bis(trifluoromethylsulfonyl) imide with $FeCl_3$
- 1-Butyl-4-methylpyridinium-bis(trifluoromethylsulfonyl) imide with $FeCl_3$
- 1-Butyl-3-methylpyridinium-bis(trifluoromethylsulfonyl) imide with $FeCl_3$
- 1,3-Dimethylimidazolium-bis(trifluoromethylsulfonyl) imide with $FeCl_3$
- 1-Ethyl-3-methylimidazolium-bis(trifluoromethylsulfonyl)imide with $FeCl_3$
- 1,3-Diethylimidazolium-bis(trifluoromethylsulfonyl) imide with $FeCl_3$
- 1-Butyl-3-methylimidazolium-bis(trifluoromethylsulfonyl)imide with $FeCl_3$
- 1-Butyl-3-ethylimidazolium-bis(trifluoromethylsulfonyl) imide with $FeCl_3$
- Trimethylammonium-bis(trifluoromethylsulfonyl)imide with $FeCl_3$
- Tetramethylammonium-bis(trifluoromethylsulfonyl) imide with $FeCl_3$
- Tetrabutylammonium-bis(trifluoromethylsulfonyl)imide with $FeCl_3$
- Tetrabutylphosphonium-bis(trifluoromethylsulfonyl) imide with $FeCl_3$
- 1-Methylpyridinium triflate with $FeCl_3$
- 1-Ethylpyridinium triflate with $FeCl_3$
- 1-Butylpyridinium triflate with $FeCl_3$
- 1,4-Dimethylpyridinium triflate with $FeCl_3$
- 1,3-Dimethylpyridinium triflate with $FeCl_3$
- 1-Ethyl-4-methylpyridinium triflate with $FeCl_3$
- 1-Ethyl-3-methylpyridinium triflate with $FeCl_3$
- 1-Butyl-4-methylpyridinium triflate with $FeCl_3$
- 1-Butyl-3-methylpyridinium triflate with $FeCl_3$
- 1,3-Dimethylimidazolium triflate with $FeCl_3$
- 1-Ethyl-3-methylimidazolium triflate with $FeCl_3$
- 1,3-Diethylimidazolium triflate with $FeCl_3$
- 1-Butyl-3-methylimidazolium triflate with $FeCl_3$
- 1-Butyl-3-ethylimidazolium triflate with $FeCl_3$
- Trimethylammonium triflate with $FeCl_3$
- Tetramethylammonium triflate with $FeCl_3$
- Tetrabutylammonium triflate with $FeCl_3$
- Tetrabutylphosphonium triflate with $FeCl_3$ This invention is illustrated by the following examples.

EXAMPLE 1

1-Ethyl-3-methylpyridinium([3-MEP]) bis(trifluoromethylsulfonyl) imide/aluminum(III)chloride ([3-MEP][$(CF_3SO_2)_2N$]/$AlCl_3$) mixtures:

A. 1:1 mixture

At room temperature while mixing slowly add 21.7 mmol $AlCl_3$ to 21.7 mmol ([3-MEP][$(CF_3SO_2)_2N$]). As a slight amount of heat is generated, the $AlCl_3$ dissolves into the melt forming a 2-phase system in which both phases are of approximately equal volume, while the lower phase is much more viscous than the upper phase. While the mixture continues to remain in two phases at 70° C., a single-phase system results at 100° C.

B. 1:2 mixture

While stirring, slowly add 43.1 mmol $AlCl_3$ to 21.7 mmol ([3-MEP][$(CF_3SO_2)_2N$]). Upon cooling to room temperature, the total amount of $AlCl_3$ that is added remains dissolved in the reaction system, while the reaction system itself, is present in two phases.

C. 1:3 mixture

While stirring, slowly add 64.2 mmol $AlCl_3$ to 21.7 mmol ([3-MEP][$(CF_3SO_2)_2N$]). A clear, homogeneous single-phase solution results, which, after cooling to room temperature, remains clear and single-phased.

D. 1:4.5 mixture

While stirring, slowly add 99.1 mmol to 21.7 mmol ([3-MEP][$(CF_3SO_2)_2N$]) at 130° C. A clear, homogeneous, single-phase solution forms and remains clear and single-phased even after cooling to room temperature.

EXAMPLE 2

1-Ethyl-4-methylpyridinium([4-MEP]) bis(trifluoromethylsulfonyl)imide/aluminum(III)chloride ([4-MEP][$(CF_3SO_2)_2N$]/$AlCl_3$) mixtures:

A. 1:1 mixture

At 90° C., while stirring add 11.7 mmol $AlCl_3$ to 11.7 mmol ([4-MEP][$(CF_3SO_2)_2N$]). A two-phase system forms in which both phases have roughly the same volume. Upon cooling, the $AlCl_3$ precipitates out of this system at temperatures below 70° C.

B. 1:2 mixture

At 70° C. while stirring add 23.2 mmol $AlCl_3$ to 11.7 mmol ([4-MEP][$(CF_3SO_2)_2N$]). A 2-phase mixture forms with the volume of the lower phase substantially smaller than that of the upper phase. No solid precipitates from this system even upon cooling to room temperature.

C. 1:3 mixture

At 105° C. while stirring add 34.3 mmol $AlCl_3$ to 11.7 mmol ([4-MEP][$(CF_3SO_2)_2N$]). A clear phase is formed, which, after cooling to room temperature remains single-phased and clear.

D. 1:4 mixture

At 130° C. while stirring add 46.6 mmol $AlCl_3$ to 11.7 mmol ([4-MEP][$(CF_3SO_2)_2N$]). A clear phase is formed, which, after cooling to room temperature remains single-phased and clear.

EXAMPLE 3

Reaction of octanoic acid chloride with 1-chloro-2-phenylethane with the ionic liquid ([3-MEP][$(CF_3SO_2)_2N$]/$AlCl_3$) (molar ratio 1:3) as the catalytically active component Under inert gas atmosphere while stirring at 105° C. 40 mmol $AlCl_3$ is slowly added to 13.3 mmol ([3-MEP][$(CF_3SO_2)_2N$]). A clear, homogeneous single-phase solution forms and remains clear and single-phase after cooling to room temperature. The resulting ionic liquid is mixed at room temperature 20 mmol octanoic acid chloride. 20 mmol 1-chloro-2-phenylethane is mixed in dropwise at room temperature. The reaction mixture is stirred for 6 hours at room temperature. The reaction mixture is carefully hydrolyzed with an excess amount of water; the aqueous phase extracted with $CH_2Cl_2$. $CH_2Cl_2$ is removed under a light vacuum, and the residue extracted with pentane. While the educts and products of the reaction dissolve in pentane, 11 mmol of the ionic liquid ([3-MEP][$(CF_3SO_2)_2N$]) is recovered as residue. Based on GC analysis, the pentane phase contains: 70.2% p-acylation product, 12.6% m-acylation product, 5.5% octanoic acid (hydrolysis product of the octanoic acid), and 4.6% 1-chloro-2-phenylethane. The processing method that was used was verified by calculating a mass balance.

The starting materials: triflate or bis(trifluoromethylsulfonyl)imide salts containing imidazolium, pyridinium, ammonium, or phosphonium ions are known.

What is claimed is:

1. An ionic liquid comprising a mixture of one or more triflate or bis(trifluoromethylsulfonyl)imide salt(s) of an ammonium, phosphonium, imidazolium, or pyridinium ion with one or more Lewis acid(s) wherein the total of the molar contents of the Lewis-acid(s) in the mixture is between a greater than 50% , wherein the Lewis acid is $AlCl_3$, $AlBr_3$, $SnCl_2$, $FeCl_3$, or $ZnCl_2$.

2. The ionic liquid of claim 1 in which the total of the molar contents of the Lewis acid(s) in the mixture is from between greater than 50% and 85%.

3. The ionic liquid of claim 2 in which the total of the molar contents of the Lewis acid(s) in the mixture is from about 67-80%.

4. The ionic liquid of claim 1 wherein the cation of the triflate or bis(trifluoromethylsulfonyl)imide salt is (1) a quaternary ammonium cation having the general formula $[NR^1R^2R^3R]^+$; (2) a phosphonium cation having the general formula $[PR^1R^2R^3R]^+$; (3) an imidazolium cation having the general formula of Formula I:

where the imidazole ring of Formula I can be substituted with one or more groups selected from the $C_1$-$C_8$ alkyl, $C_6$-$C_{12}$-aryl, or $C_5$-$C_{12}$-aryl-$C_1$-$C_6$ alkyl groups; (4) pyridinium cations of the general formula of Formula II:

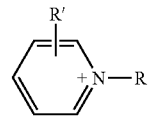

where the pyridine ring of Formula II can be substituted with one or more groups comprising the $C_1$-$C_8$ alkyl, or $C_6$-$C_{12}$-aryl, or $C_5$-$C_{12}$-aryl-$C_1$-$C_6$ alkyl groups; and the substituents R, R', $R_1$, $R_2$, $R_3$ are selected independently of each other from the group comprising hydrogen; linear or branched, saturated or unsaturated, aliphatic or alicyclic alkyl groups having 1 to 20 carbon atoms: and aryl, aryl-$C_1$-$C_6$ alkyl groups having 6 to 12 carbon atoms in the aryl moiety, which may optionally be substituted with at least one $C_1$-$C_6$ alkyl group.

5. The ionic liquid of claim 1, wherein the Lewis acid is $AlCl_3$.

6. The ionic liquid of claim 1, wherein the Lewis acid is $FeCl_3$.

7. A process for preparing the ionic liquid of claim 1 comprising proportionally adding the Lewis acid(s) to the triflate or bis(trifluoromethylsulfonyl)imide salt(s) while stirring at temperatures from 0 to 300° C., preferably from 20 to 180° C., more preferably from 50 to 150° C., to yield the ionic liquid as a liquid-liquid multiple-phase system.

8. A method of catalyzing a Lewis acid-catalyzed reaction comprising the step of using an ionic liquid of claim 1.

9. The method of claim 8, wherein said reaction is selected from the group consisting of Friedel-Crafts alkylation reactions, Friedel-Crafts acylation reactions, alkylation reactions, carbonylization reactions, isomerization reactions, and oligomerization reactions.

* * * * *

UNITED STATES PATENT AND TRADEMARK OFFICE
CERTIFICATE OF CORRECTION

PATENT NO.         : 7,691,180 B2
APPLICATION NO.    : 10/564258
DATED              : April 6, 2010
INVENTOR(S)        : Wasserscheid et al.

Page 1 of 1

It is certified that error appears in the above-identified patent and that said Letters Patent is hereby corrected as shown below:

In Column 8, line 18, the portion of claim 1 reading "between a" should be deleted.

Signed and Sealed this
Eighteenth Day of October, 2011

David J. Kappos
*Director of the United States Patent and Trademark Office*